United States Patent [19]

Bloomfield

[11] 3,979,201

[45] Sept. 7, 1976

[54] CHEMICAL REGULATION OF PLANT GROWTH

[75] Inventor: Jordan J. Bloomfield, St. Louis, Mo.

[73] Assignee: Monsanto Company, St. Louis, Mo.

[22] Filed: Nov. 18, 1974

[21] Appl. No.: 524,583

Related U.S. Application Data

[62] Division of Ser. No. 275,129, July 26, 1972, Pat. No. 3,873,568.

[52] U.S. Cl. ........................................ 71/91; 71/76
[51] Int. Cl.$^2$............................................ A01N 9/12
[58] Field of Search ................ 71/91, 76; 260/332.1

[56] References Cited
UNITED STATES PATENTS
2,898,205    8/1959    Pyne ....................................... 71/91

OTHER PUBLICATIONS

Shaikhrazieva et al., "Photoinitiation of the Addition etc.;" (1971), Zh. Org. Chimii. 7, p. 1831 (1972).

Primary Examiner—Glennon H. Hollrah
Attorney, Agent, or Firm—Richard H. Shear; Donald W. Peterson

[57]    ABSTRACT

Effective plant growth regulation is obtained by the application of 3-thiabicyclo(3.2.0)heptane-6,7-dicarboxylic anhydride 3,3-dioxide to plants.

7 Claims, No Drawings

CHEMICAL REGULATION OF PLANT GROWTH

This is a division of application Ser. No. 275,129 filed July 26, 1972, now U.S. Pat. No. 3,873,568.

This invention relates to a new composition of matter which is an adduct of 2,5-dihydrothiophene 1,1-dioxide and to the use of said adduct for regulating the natural growth or development of plants. More particularly, this invention relates to 3-thiabicyclo(3.2.0)heptane-6,7-dicarboxylic anhydride 3,3-dioxide, its use for regulating plant growth or development and as the essential active ingredient in plant growth regulating compositions.

An embodiment of this invention is the novel chemical compound, 3-thiabicyclo(3.2.0)heptane-6,7-dicarboxylic anhydride 3,3-dioxide, which can be prepared by the photochemical reaction of 2,5-dihydrothiophene 1,1-dioxide with maleic anhydride. The reaction is carried out with a solution of the reactants in a suitable solvent in the presence of a sensitizer. Suitable solvents include acetone, dioxane, ethyl acetate, acetonitrile and the like. Suitable sensitizers include acetophenone, benzophenone, triphenylene and the like.

The preparation of the chemical compound of this invention can be shown as follows:

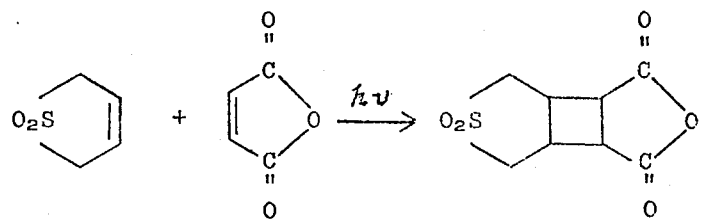

The reaction is carried out with cooling using an adequate source of ultraviolet radiation such as an Hanovia lamp (Hanovia Lamp Division, (Canrad Precision Industries).

Further details of the preparation of the chemical compound of this invention are set forth hereinafter in Example 1.

In accordance with the instant invention it has been found that desirable regulation of natural plant growth or development is achieved by the application of 3-thiabicyclo (3.2.0)heptane-6,7-dicarboxylic anhydride 3,3-dioxide to dicotyledonous plants in various stages of development. Accordingly, in the practice of this invention the chemical can be applied to the plant in the seedling stage, flowering stage, fruiting stage or maturing stage and the like or can be applied to plants at more than one stage of development. Such application may be made directly to one or more of the plant's parts, such as, roots, stems, leaves, flowers, fruits or the like or application can be made indirectly as by treatment of the growth medium of the plant such as the soil.

As employed herein, the term "natural growth or development" designates the normal life cycle of the plant in accordance with its genetics and its environment, in the absence of artificial, external influences. As may be expected, and as well understood by those skilled in the art, the effective plant regulating amount employed in the practice of this invention will vary with the regulatory effect to be achieved, the species of plant being treated and its stage of development and whether a permanent, transient or sequential regulating effect is sought. Other factors which may bear upon the determination of an appropriate plant regulating amount include the plant growth medium, the manner in which the treatment is to be applied, weather conditions such as temperature or rainfall, and the like.

Regulation of the natural growth or development of plants by chemical treatment may result from the effect of the chemical substance on the physiological processes of the plant, or it may be due to the effect of such substance on the morphology of the plant. As should be readily apparent, said regulation may also result from a combined or sequential effect of the chemical in the areas of both physiology and morphology.

In general, regulation of the natural growth or development which leads to a morphological change in the plant is readily noticeable by visual observation. Such changes can be found in the size, shape, color or texture of the treated plant of any of its parts. Similarly, changes in the quantity of plant fruit or flowers can be simply noted.

On the other hand, regulation which leads to changes in the physiological processes occur within the treated plant and are usually hidden from the eye of an observer. Changes of this type are most often in the production, location, storage or use of naturally occurring chemicals, including hormones, within the plant. Physiological changes in a plant may be recognized when followed by a subsequent change in morphology. Additionally, there are numerous analytical procedures known to those skilled in the art for determining the nature and magnitude of changes in the various physiological processes.

The compound of the instant invention serves to regulate the natural growth or development of treated plants in a number of diverse ways, and it is to be understood that the compound may not produce identical regulatory effects on each plant species or at every rate of application. As stated above, responses will vary in accordance with the rate, the plant, etc.

A regulatory response demonstrated by the chemical useful in the practice of this invention can be generally termed retardation of vegetative growth and such a response has a wide variety of beneficial features. In certain plants this retardation of vegetative growth causes a diminution or elimination of apical dominance leading to a shorter main stem and increased lateral branching. This regulation of the natural growth or development of plants produces smaller, bushier plants which often demonstrate increased resistance to drought, lodging, temperature extremes, pest infestations and the like. Thus, the method of this invention provides for plants that are in a good state of health and tends to produce more vigorous plants.

In many types of plants, such as potatoes, sugar beets, grapes, melons and fruit trees, the retardation of vegetative growth by chemical treatment results in an increase in the carbohydrate content of the plants at harvest. It is believed that by retarding or suppressing such growth at the appropriate stage of development, less of the available carbohydrate is consumed as plant food with a consequent enhancement of the starch and/or sucrose content.

Also with fruit trees, such as in apple orchards, retardation of vegetative growth is demonstrated by shorter branches which lead to more fullness in shape and may also result in lesser vertical elongation. These factors contribute to the ease of access to the orchard and simplify the fruit harvesting procedure.

As illustrated in the examples which are hereinafter presented, the chemical compound of this invention regulates the natural growth or development of treated plants in numerous other and different respects. Particularly advantageous among these other regulatory effects is the improvement in fruit or pod set. Although regulatory effects such as those described above can be desirable, often it is the ultimate result of these effects upon the economic factor which is of primary significance in crop plants or upon the aesthetic factor in ornamental plants. Thus, it must be recognized that increases in yield of individual plants, increases in the yield per unit of cropping area, improvement in the quality of the plants' product, improvement in the plants' vigor and reductions in the cost of harvesting and/or subsequent processing are all to be considered in any assessment of the consequence of an individual regulatory effect during the growth or development of a plant.

In practicing the plant regulating methods of this invention the chemical generally is applied to plants in the form of a composition containing one or more materials referred to in this art as an adjuvant in liquid or solid form. Suitable plant regulating compositions are prepared by admixing the chemical with an adjuvant including diluents, extenders, carriers, surfactants, foaming agents and conditioning agents to provide compositions in the form of finely divided particulate solids, granules, pellets, wettable powders, dusts, solutions, foams and aqueous dispersions or emulsions. Thus, 3-thiabicyclo(3.2.0)heptane-6,7-dicarboxylic anhydride 3,3-dioxide (active ingredient) can be used with an adjuvant such as a finely divided particulate solid, a solvent liquid of organic origin, water, a foaming agent, a surface active agent, such as, wetting agents, dispersing agents, suspending agents and emulsifying agents or any suitable combination of such adjuvants. Compositions containing the chemical and a surface active agent are preferred and provide concentrates suitable for further dilution prior to application.

In selecting the appropriate rate of application of the active ingredient it will be recognized that precise dosages will be dependent upon the plant species being treated, the particular plant part or habitat to which application is made, the development stage of the plant, the mode of application, such as soil incorporation, band application, broadcast application, foliar application and various other factors known to those skilled in the art. In foliar treatment for the regulation of plant growth, the active ingredient is applied in amounts from about 0.05 to about 20 or more pounds per acre. Foliar applications of from 1 to 15 pounds of the active ingredient per acre are preferred. In applications to the soil habitat of seedlings and established vegetation for the regulation of plant growth, the active ingredient is applied in amounts of from about 0.1 to about 30 pounds per acre or more. Preferably, the active ingredient is applied to the soil at a rate of from 1 to 20 pounds per acre. Foliar application to plants at the blooming stage, e.g. 10% blossoms, are particularly advantageous and are preferred.

The preparation of 3-thiabicyclo(3.2.0)heptane-6,7-dicarboxylic anhydride 3,3-dioxide useful as the essential active ingredient in the plant growth regulating compositions of this invention is illustrated in the following example.

EXAMPLE 1

Approximately 147 g. (1.5 moles) maleic anhydride, 177 g. (1.5 moles) 2,5-dihydrothiophene 1,1-dioxide and 14 g. acetophenone were dissolved in 5 liters of acetone in a 5 liter three neck flask. The flask was fitted with a nitrogen bubbler and quartz water cooled immersion well containing a 450 watt Hanovia lamp and a Pyrex glass filter. The third neck was connected to a tube leading to an exhaust hood. The entire apparatus was wrapped in aluminum foil and immersed in a cold bath so that internal temperature was 5°–6°C. Nitrogen was bubbled vigorously for one hour and then under moderate nitrogen flow the light was turned on. After twelve days the precipitated product was filtered off and washed with acetone to yield about 197 g. of 3-thiabicyclo(3.2.0)heptane-6,7-dicarboxylic anhydride 3,3-dioxide a white solid m.p. 293°–296°C., identified by nuclear magnetic resonance and IR analysis, IR spectrum (cm$^{-1}$): 1855, 1775.

The preparation of this compound has been recently reported by V. Sh. Shaikhrazieva et al. *Zhurnal Organicheskei Khimii*, Vol. 7, No. 8, p. 1763, August 1971.

The useful and unexpected plant growth regulating properties of 3-thiabicyclo(3.2.0)heptane-6,7-dicarboxylic anhydride 3,3-dioxide is demonstrated by exemplary tests set forth below. In the following tests this chemical was applied an an aqueous composition at the equivalent rate of active ingredient indicated. The aqueous compositions were prepared by solubilizing the required amount of the chemical in a volume of acetone which is further admixed with a like volume of 0.05% by weight aqueous solution of dioctyl sodium sulfosuccinate, surface active agent, to provide sufficient composition which is applied at the rate equivalent to 200 gallons per acre to apply the active ingredient at the equivalent rate indicated.

EXAMPLE 2

A number of soybean plants are grown from seed in aluminum pans in a greenhouse for a period of approximately one week to the primary leaf stage. The plants are thinned to three uniform plants in each pan and the height of each plant is measured to the terminal bud and the average height is noted. One pan containing three soybean plants is used for each chemical treatment and four pans are not treated and used as a control. The aqueous composition of the chemical is then applied to the pan of growing plants by overhead spray at an established rate expressed as pounds per acre. The treated pans along with the control pans, are watered from below, fertilized and otherwise maintained in a greenhouse under uniform growth conditions. Two weeks after application of the chemical the average height of the plants in the treated pan is determined as above and the difference in the average height before and 2 weeks after application represents the development of the treated plants. This development in growth of the treated plants is compared to the average development in growth of the plants in the control pans during the same period of time. A variation of 25% or more in the development of at least two-thirds of the treated plants when compared to the development of the control plants demonstrates that the chemical is effective for regulating the natural growth or development of the plants. Accordingly, a chemical is considered effective when the treated plants manifest at least a 25% decrease in height development when compared to the untreated control plants, i.e. retardation of vegetative growth.

Using the procedure of Example 2, 3-thiabicyclo (3.2.0)heptane-6,7-dicarboxylic anhydride 3,3-dioxide demonstrated effective retardation of vegetative growth when applied to the plants at the primary leaf stage at a rate equivalent to about 6 pounds per acre.

EXAMPLE 3

In this evaluation soybean plants growing in individual pots which were 4 weeks old (3-4 trifoliate stage) and 6 weeks old (5-6 trifoliate stage) were used for each application of chemical. An overhead spray of an aqueous composition of the chemical is applied to 2 pots at each growth stage at an equivalent rate as indicated below. Two to four sets of plants which receive no chemical application are included and serve as controls. All of the pots are maintained under good growing conditions and are watered and are uniformly fertilized under uniform conditions. Two weeks after the application of the chemical the growth response of the treated plants are compared with that of the control plants. The total height of the plant is measured to the tip of the terminal bud. A variation of 15% or more in the average total height of the treated plants, when compared to that of the control plants, demonstrates that the chemical is effective for regulating the natural growth or development of the plants.

Employing the procedure of Example 3 an application of the compound of this invention at a rate equivalent to about 5 pounds per acre to plants 6 weeks old at the time of treatment elicited a growth response in the plants resulting in plants reduced in height in excess of 15%. An application of the compound at this 5 pounds per acre rate to plants 4 weeks old at the time of treatment did not reduce the total height of the treated plants by 15% indicating that the degree of response in the plant from chemical treatment is dependent not only on the amount of the chemical applied but also on the stage of development of the plant at time of treatment. This variation in plant response to chemical treatment is well recognized since it is the nature of plants to have different growth rates at various stages of development throughout the life cycle of the plant.

EXAMPLE 4

Soybean plants growing in sample plots in the field with about 9 plants per row foot and 30 inch rows (normal population density) and about 9 plants per row foot and 12 inch rows (excessive population density) were used to evaluate the effect of chemical treatment upon the yield of the plants. The plants were treated early in the flowering stage, i.e. approximately 10% blooms, with an aqueous composition of 3-thiabicyclo (3.2.0)heptane-6,7-dicarboxylic anhydride 3,3-dioxide using an overhead spray to apply the chemical at rates equivalent to about 4 and 8 pounds per acre to the plants in the 30 inch rows and at rates equivalent to about 10 and 20 pounds per acre to the plants in 12 inch rows. These rates of applications did not significantly alter the height of the treated plants. At harvest the pod number and seed yield of the treated plants was compared to that of untreated control plants growing under the same conditions and at the same population density. The plants in the 30 inch rows treated with the chemical at a rate equivalent to about 4 pounds per acre demonstrated an improvement in pod number and weight of seed yield in excess of 10%. The plants in 12 inch rows treated at a rate equivalent to about 10 pounds per acre demonstrated an improvement in pod number and weight of seed yield in excess of 15% over the high population controls. The plants in both the 30 inch rows and 12 inch rows treated at the higher rates of application for each population density showed less improvement in the pod number and weight of seed yields. The plants in the 12 inch rows treated with the chemical at a rate equivalent to about 20 pounds per acre demonstrated an improvement in pod number and weight of seed yield greater than 5%. Thus, the improvement in the yield of plants treated in accordance with this invention is particularly advantageous for obtaining higher yields per unit of cropping area.

From the illustrative examples above it should be clear that the regulatory response will be dependent upon the rate of application, the plant specie and its stage of development and other factors well understood by those skilled in the art.

In utilizing the method of this invention it is advantageous to treat dicotyledonous crops planted at excessive populations per unit area with an effective amount of the chemical of this invention to elicit a growth response in the plant which compensates for the overcrowding in the field. Illustrative dicotyledonous crop plants which can be treated in accordance with this invention are cotton (Gossypium), soybean (Glycine), beans (Phaseolus), tomato (Hycopersieum), beet (Beta), potato (Solanum), coffee (Coffea) and the like.

The methods of this invention can be conveniently carried out in conjunction with agronomic practices such as treating the plants with insecticides, fungicides, nematocides, fertilizer and the like. The application of compositions containing the chemical compound of this invention and other agricultural chemicals such as selective herbicides, insecticides, fungicides, fertilizers, nematocides and the like are particularly advantageous for obtaining the desired results with minimum treatment costs.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

The embodiments of the invention in which an exclusive property or privilege is claimed are defined as follows:

1. A method of regulating the natural growth or development of dicotyledonous plants which comprises treating said plants with an effective plant-regulating amount of 3-thiabicyclo(3.2.0)heptane-6,7-dicarboxylic anhydride 3,3-dioxide.

2. The method of claim 1 wherein said plants are field crops.

3. The method of claim 2 wherein the plants are treated at a rate of from about 0.1 to about 20 pounds per acre.

4. The method of claim 1 wherein said plants are treated with a yield enhancing amount of 3-thiabicyclo(3.2.0)heptane-6,7-dicarboxylic anhydride 3,3-dioxide.

5. The method of claim 4 wherein said plants are soybean plants.

6. The method of claim 5 wherein the soybean plants are treated at a rate of about 4 to 10 pounds per acre when the plants are beginning to bloom.

7. A plant growth regulating composition comprising a surface active agent and an effective amount of 3-thiabicyclo (3.2.0)heptane-6,7-dicarboxylic anhydride 3,3-dioxide.

* * * * *